United States Patent
Pugh

(10) Patent No.: US 8,640,916 B2
(45) Date of Patent: *Feb. 4, 2014

(54) SENSOR DISPENSER DEVICE AND METHOD OF USE

(75) Inventor: Jerry T. Pugh, Santa Rosa, CA (US)

(73) Assignee: LifeScan, Inc., Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/093,941

(22) Filed: Apr. 26, 2011

(65) Prior Publication Data

US 2011/0198367 A1    Aug. 18, 2011

Related U.S. Application Data

(63) Continuation of application No. 11/138,079, filed on May 25, 2005, now Pat. No. 8,016,154.

(51) Int. Cl.
| | |
|---|---|
| *B23Q 7/00* | (2006.01) |
| *B65G 59/00* | (2006.01) |
| *B65D 83/00* | (2006.01) |
| *G01R 1/20* | (2006.01) |

(52) U.S. Cl.
USPC .............. 221/239; 221/227; 221/191; 221/28

(58) Field of Classification Search
USPC ............... 221/227, 22–23, 267, 28, 191, 239, 221/312 C
See application file for complete search history.

(56) References Cited

U.S. PATENT DOCUMENTS

| | | |
|---|---|---|
| 4,088,448 A | 5/1978 | Lilja et al. |
| 4,142,863 A | 3/1979 | Covington et al. |
| 4,476,149 A | 10/1984 | Poppe et al. |
| 4,554,064 A | 11/1985 | McClintock et al. |
| 4,578,716 A | 3/1986 | van Rijckevorsel et al. |
| 4,852,025 A | 7/1989 | Herpichbohm et al. |
| 5,053,199 A | 10/1991 | Keiser et al. |
| 5,108,564 A | 4/1992 | Szuminsky et al. |
| 5,120,420 A | 6/1992 | Nankai et al. |
| 5,171,689 A | 12/1992 | Kawaguri et al. |
| 5,312,590 A | 5/1994 | Gunasingham |
| 5,325,853 A | 7/1994 | Morris et al. |
| 5,366,609 A | 11/1994 | White et al. |

(Continued)

FOREIGN PATENT DOCUMENTS

| | | |
|---|---|---|
| AU | 5487394 A | 8/1994 |
| DE | 3103484 | 8/1982 |

(Continued)

OTHER PUBLICATIONS

European Search Report No. EP 03 00 7604 dated May 19, 2003.

(Continued)

*Primary Examiner* — Michael K Collins
(74) *Attorney, Agent, or Firm* — Hiscock & Barclay, LLP

(57) ABSTRACT

Disclosed herein are electrochemical sensor dispensing methods and apparatus. The sensors dispensers can include an elongate body having a proximal end and a distal, the elongate body including a proximally positioned dispensing surface with an opening for dispensing a sensor. A storage chamber having a series of connected sensors is positioned distally and can feed a proximally positioned sensor feeder mechanism. The feeder mechanism includes an elongate member having a first end and second end, the second end adapted to pivot between a sensor engaging position and a sensor feeding position.

25 Claims, 6 Drawing Sheets

(56) References Cited

U.S. PATENT DOCUMENTS

| | | | |
|---|---|---|---|
| 5,395,504 A | 3/1995 | Saurer et al. | |
| 5,399,256 A | 3/1995 | Bohs et al. | |
| 5,505,308 A | 4/1996 | Eikmeier et al. | |
| 5,525,297 A | 6/1996 | Dinger et al. | |
| 5,609,823 A | 3/1997 | Harttig et al. | |
| 5,628,890 A | 5/1997 | Carter et al. | |
| 5,679,311 A | 10/1997 | Harttig et al. | |
| 5,797,693 A | 8/1998 | Jaeger et al. | |
| 5,856,195 A | 1/1999 | Charlton et al. | |
| 5,880,829 A * | 3/1999 | Kauhaniemi et al. | 356/246 |
| 5,904,898 A | 5/1999 | Markart | |
| 5,942,102 A | 8/1999 | Hodges et al. | |
| 5,989,917 A | 11/1999 | McAleer et al. | |
| 6,027,689 A | 2/2000 | Markart et al. | |
| 6,176,119 B1 | 1/2001 | Kintzig et al. | |
| 6,180,063 B1 | 1/2001 | Markart | |
| 6,193,873 B1 | 2/2001 | Ohara et al. | |
| 6,251,260 B1 | 6/2001 | Heller et al. | |
| 6,284,125 B1 | 9/2001 | Hodges et al. | |
| 6,299,757 B1 | 10/2001 | Feldman et al. | |
| 6,378,702 B1 | 4/2002 | Kintzig et al. | |
| 6,413,410 B1 | 7/2002 | Hodges et al. | |
| 6,475,372 B1 | 11/2002 | Ohara et al. | |
| 6,676,995 B2 | 1/2004 | Dick et al. | |
| 6,689,411 B2 | 2/2004 | Dick et al. | |
| 6,716,577 B1 | 4/2004 | Yu et al. | |
| 6,749,887 B1 | 6/2004 | Dick et al. | |
| 6,780,645 B2 | 8/2004 | Hayter et al. | |
| 6,827,899 B2 | 12/2004 | Maisey et al. | |
| 6,830,934 B1 | 12/2004 | Harding et al. | |
| 6,952,950 B2 | 10/2005 | Doe et al. | |
| 6,997,343 B2 | 2/2006 | May et al. | |
| 7,063,234 B2 | 6/2006 | Giraud et al. | |
| 7,178,416 B2 | 2/2007 | Whelan et al. | |
| 7,449,148 B2 | 11/2008 | Matsumoto et al. | |
| 7,582,262 B2 | 9/2009 | Funke et al. | |
| 7,628,292 B2 | 12/2009 | Lancesseur et al. | |
| 7,723,113 B2 * | 5/2010 | Charlton | 436/46 |
| 8,001,825 B2 | 8/2011 | Pugh et al. | |
| 8,016,154 B2 * | 9/2011 | Pugh | 221/23 |
| 8,153,080 B2 * | 4/2012 | Kheiri et al. | 422/401 |
| 2002/0057993 A1 | 5/2002 | Maisey et al. | |
| 2002/0104849 A1 | 8/2002 | Giruad | |
| 2002/0150501 A1 | 10/2002 | Robertson et al. | |
| 2003/0032190 A1 | 2/2003 | Brown et al. | |
| 2003/0089730 A1 | 5/2003 | May et al. | |
| 2003/0116583 A1 | 6/2003 | Pugh | |
| 2003/0175155 A1 | 9/2003 | Charlton | |
| 2003/0185708 A1 | 10/2003 | Otake | |
| 2003/0186446 A1 | 10/2003 | Pugh | |
| 2003/0191415 A1 * | 10/2003 | Moerman et al. | 600/584 |
| 2003/0223906 A1 | 12/2003 | McAllister et al. | |
| 2004/0007585 A1 | 1/2004 | Griffith et al. | |
| 2004/0050717 A1 | 3/2004 | Teodorczyk et al. | |
| 2004/0178216 A1 | 9/2004 | Brickwood et al. | |
| 2005/0118071 A1 | 6/2005 | Sacherer | |
| 2005/0186162 A1 | 8/2005 | Sato | |
| 2005/0240369 A1 | 10/2005 | Diorio et al. | |
| 2005/0240370 A1 | 10/2005 | Diorio et al. | |
| 2005/0281706 A1 | 12/2005 | Funke et al. | |
| 2006/0104861 A1 | 5/2006 | Windus-Smith et al. | |
| 2006/0226985 A1 | 10/2006 | Goodnow et al. | |
| 2007/0034630 A1 | 2/2007 | Lancesseur et al. | |
| 2007/0172388 A1 | 7/2007 | Padmanabhan et al. | |
| 2007/0208308 A1 | 9/2007 | Gibson et al. | |
| 2007/0233395 A1 | 10/2007 | Neel et al. | |
| 2008/0021296 A1 * | 1/2008 | Creaven | 600/365 |
| 2008/0068197 A1 | 3/2008 | Neubauer et al. | |
| 2008/0114228 A1 | 5/2008 | McCluskey et al. | |
| 2008/0164280 A1 | 7/2008 | Kuriger et al. | |
| 2008/0208042 A1 | 8/2008 | Ortenzi et al. | |
| 2009/0159444 A1 | 6/2009 | Ghesquiere et al. | |
| 2009/0178937 A1 | 7/2009 | Taylor | |

FOREIGN PATENT DOCUMENTS

| | | |
|---|---|---|
| DE | 3708031 | 11/1987 |
| EP | 0290770 A2 | 11/1988 |
| EP | 0400918 | 12/1990 |
| EP | 0609760 A1 | 8/1994 |
| EP | 0735363 A1 | 10/1996 |
| EP | 0-928967 A2 | 7/1999 |
| EP | 1-081490 A1 | 3/2001 |
| JP | 3167464 A | 7/1991 |
| JP | 0434306 | 11/1992 |
| JP | 5002007 A | 1/1993 |
| JP | 6222874 | 8/1994 |
| SU | 1351627 A | 11/1987 |
| SU | 1351627 A2 | 11/1987 |
| WO | WO-94/19684 A1 | 9/1994 |
| WO | WO-9429731 A1 | 12/1994 |
| WO | WO-99/32881 A1 | 7/1999 |
| WO | WO-99/60391 A1 | 11/1999 |
| WO | WO-02/26129 A1 | 4/2002 |
| WO | WO-03/085392 A1 | 10/2003 |

OTHER PUBLICATIONS

Osamu, Niwa, et al. "Electrochemical Behavior of Reversible Redox Species at Interdigitated Array Electrodes with Different Geometries: Consideration of Redox Cycling and Collection Efficiency", Analytical Chemistry; Mar. 1990, vol. 62, No. 5, pp. 447-452.

* cited by examiner

SENSOR DISPENSER DEVICE AND METHOD OF USE

CROSS-REFERENCE TO RELATED APPLICATION

This application is a continuation of U.S. patent application Ser. No. 11/138,079, filed May 25, 2005, entitled "SENSOR DISPENSER DEVICE AND METHOD OF USE", which is hereby incorporated by reference herein in its entirety.

BACKGROUND OF THE INVENTION

Analyte detection in physiological fluids, e.g. blood or blood-derived products, is of ever increasing importance to today's society. Analyte detection assays find use in a variety of applications, including clinical laboratory testing, home testing, etc., where the results of such testing play a prominent role in diagnosis and management in a variety of disease conditions. Analytes of interest include glucose for diabetes management, cholesterol, and the like. In response to this growing importance of analyte detection, a variety of analyte detection protocols and devices for both clinical and home use have been developed.

One type of system that allows people to conveniently monitor their blood glucose levels includes a sensor (e.g., a disposable test strip), for receive a blood sample for a user, and a meter that "reads" the test strip to determine the glucose level in the blood sample. The test strip typically includes an electrical contact area at one end for mating with the meter and a sample chamber at the other end that contains reagents (e.g., glucose oxidase and a mediator) and electrodes. To begin the test, the test strip is inserted into the meter and the user applies a blood sample to the sample chamber. The meter then applies a voltage to the electrodes to cause a redox reaction and the meter measures the resulting current and calculates the glucose level based on the current. After the test, the test strip can be disposed.

It should be emphasized that frequent measurements of blood glucose levels may be critical to the long-term health of many users. As a result, there is a need for blood glucose measuring systems that are easy to use. One improvement in blood glucose monitoring has been a reduction in the volume of sample needed to perform a test, which reduces the trauma associated acquiring blood samples. However, as sample sizes become smaller, the dimensions of the sample chamber and electrodes in the test strip also become smaller. This, in turn, may make test strips become more difficult to handle.

One solution has been the use of cassettes that hold a series of test strips (e.g., a dozen) that can be mechanically fed from the cassette into a meter without handling by a user. For example, one such cassette has a circular configuration with axially positioned test strips, through a complicated mechanized procedure, individual test strips are rotated into position and fed into the meter. Unfortunately, such systems can require complex mechanical structures that result in added expense and unwanted bulk.

Accordingly, there is a need to for blood glucose measuring systems with features for measuring blood glucose levels conveniently and reliably.

SUMMARY OF THE INVENTION

The present invention generally provides methods and apparatus for electrochemically determining an analyte concentration in a physiological sample. In one aspect, described herein, an electrochemical sensor dispenser device is disclosed. The device comprises an elongate body having a proximal and a distal end, with a proximally positioned dispensing surface having an opening for dispensing a sensor. The elongate body houses a storage chamber that stores a series of electrochemical sensors and sensor feeder mechanism that can dispense the sensors to a meter.

In one embodiment, the feeder mechanism includes an elongate engaging member having a first end and second end, the second end adapted to move between a sensor engaging position and a sensor feeding position. For example, the elongate member can be pivotally secured at the first end to the elongate body of the sensor dispenser. Alternatively, the elongate member is fixedly secured at the first end and is flexible. To dispense a sensor, the feeder mechanism is shifted from the sensor engaging position to the sensor feeding position.

In one aspect, the sensor dispenser is adapted for use with a meter such that engaging the dispenser with a meter causes the elongate member to move from the sensor dispensing position to the sensor feeding position. In the sensor feeding position, the meter can remove a sensor from the dispenser.

To facilitate sensor dispensing, the sensor dispenser and/or meter can include alignment features. These features assist a user with orienting the dispenser and meter, and can also help to align the sensor feeding mechanism with a sensor mating mechanism on the meter. In one aspect, the sensor dispenser includes a portion that extends beyond the sensor feeding mechanism to provide an alignment surface. The alignment surface can contact a complementary surface on the meter. A guide blade on the dispenser can also facilitate alignment. For example, a guide blade extending from a proximal surface of the dispenser can be received in a recess within the meter.

The sensors used with the sensor dispenser can be connected to one another via a flexible connection. In the storage chamber, the flexible connection allows the sensors to be configured in a space-saving folded condition and then be pivoted into position for dispensing. To protect the sensors, the elongate body can provide a generally airtight enclosure. When a user wishes to dispense a sensor, a resealable opening at the proximal end of the elongate body can be opened.

In one aspect, the sensors are electrochemical sensors having a longitudinally extending reaction chamber defined by opposed electrodes. Laterally spaced electrical contact areas positioned on the surface of the sensor can mate with the meter to allow the meter to electrically communicate with the electrodes. The sensors can also have mating features for engaging with the feeding mechanism of the sensor dispenser and/or with the sensor mating mechanism of the meter. In one aspect, the mating feature is an open area in which the elongate member can sit when positioned in the sensor engaging position.

In another embodiment, a system for delivering an electrochemical sensor to a meter is disclosed, including a sensor dispenser having a sensor storage area and a sensor dispensing mechanism. The sensor dispenser mechanism includes an elongate member that can move between a sensing dispensing position and a sensor engaging position. The system further includes a meter adapted to receive a sensor, the meter including a surface adapted to engage the sensor dispensing mechanism and move the elongate member from a sensor dispensing position to a sensor engaging position.

Methods of using the sensor dispenser are also disclosed herein. In one aspect, an array of connected sensors is positioned within a sensor dispenser having a feeding mechanism that holds a first sensor in place. Insertion of a meter into the dispenser actives the feeder mechanism. For example, contacting the feeder mechanism with the meter releases the sensor from the feeder mechanism, while a mating mechanism on the meter engages the sensor. As the sensor is released from the dispenser, the mating mechanism locks the sensor within the meter. Separating the meter from the dispenser can tear the sensor away from the array of connected sensors and can pull the next sensor into engagement with the feeder mechanism.

Once the sensor is mated with the meter, a user can deliver a sample of physiological fluid to the sensor and perform an analysis. In one aspect, the sensor and the meter are used to determine the concentration of glucose in whole blood. The user delivers a sample (e.g., a whole blood sample) into a reaction chamber within the sensor, the reaction chamber having a reagent and electrodes. The meter creates an electrical potential across the electrodes and collects data (e.g., time and current data). Based on the collected data the meter can provide the user with information about an analyte within the sample (e.g., glucose concentration). After completion of a test, the sensor can be ejected from the meter.

DETAILED DESCRIPTION

Disclosed herein, are sensor dispensing methods and devices suited for the storage and/or delivery of a wide variety of electrochemical sensors, such as, sensors suited for use in the determination of analytes in whole blood or derivatives thereof. In one aspect, the sensor dispenser can store an array of such sensors and can dispense individual sensors for receipt by a meter. Also disclosed herein are sensor dispensing systems that include a meter adapted to mate with the sensor dispenser and to receive sensors therefrom. In one aspect, when the meter engages the sensor dispenser, a feeding mechanism on the sensor dispenser is activated and a sensor is dispensed.

Figure 1:
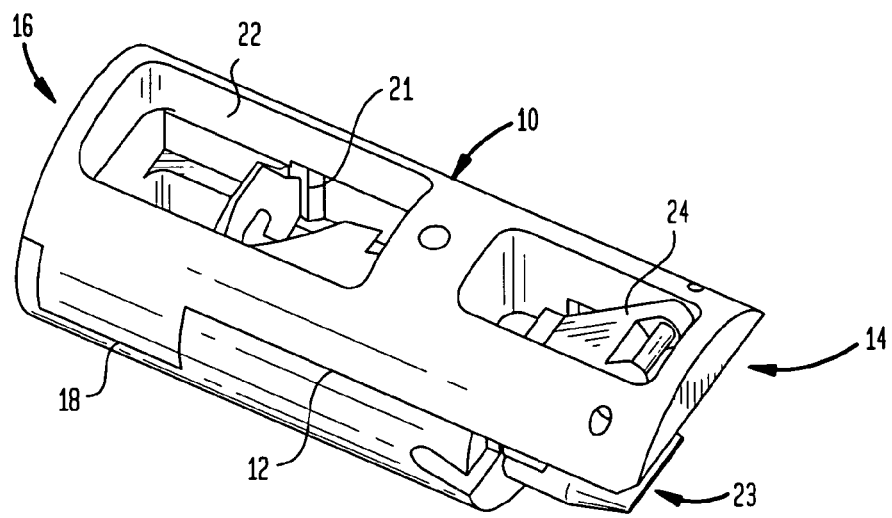
FIG. 1 is a perspective view of one embodiment of the sensor dispenser disclosed herein.

In one embodiment, the dispenser described herein includes an elongate body containing a distal sensor storage chamber, adapted to hold at least one electrochemical sensor (e.g., an array of connected sensors), and a proximal sensor feeder mechanism adapted to deliver a sensor to a meter. One exemplary embodiment of sensor dispenser 10 adapted to dispense an array of sensors is illustrated in FIG. 1, and includes an elongate body 12 having a proximal end 14 and a distal end 16. The distal portion of elongate body 12 can include a storage area 18 for holding an array of connected sensors 20. In particular, a series of folded sensors can be positioned with a cavity 22 and then individual dispensed from a proximally positioned feeder mechanism 24. While the sensor storage area is described as "distal" herein and the feeder mechanism is described as "proximal," these terms are used for convenience. On skilled in the art will appreciate that the location of the feeder mechanism will depend on the orientation of the sensor dispenser and could be positioned in any location adjacent to the storage chamber which would allow dispensing of the sensors (e.g., on top of, distally to, etc.).

Figure 2A:
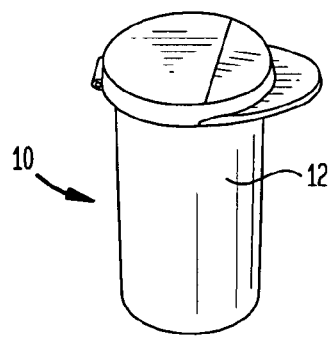
FIG. 2A is a perspective view of another embodiment of the sensor dispenser including a resealable opening.
Figure 2B:
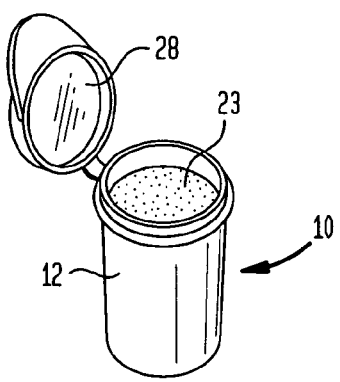
FIG. 2B is a perspective view of the sensor dispenser of FIG. 2A open at one end.

Body 12 can have a variety of shapes including, for example, a generally cylindrical shape as shown in the FIGS. One skilled in the art will appreciate a variety of alternative shapes capable of defining storage area 18 and feeder mechanism 24 could be used. Body 12 can include features to protect sensors positioned within sensor dispenser 10. For example, body 12 can enclose storage area 18 and feeder mechanism 24 in a protective shell, as shown in FIGS. 2A and 2B, to shield sensors 20 positioned therein from the environment. For example, body 12 can define a resealable chamber that limits exposure of sensors 20 to the atmosphere. When a user wishes to dispense a sensor, body 12 is opened via a resealable flap 28 to expose a proximally positioned dispensing surface 23. After dispensing a sensor, body 12 is closed to provide a generally airtight container. One skilled in the art will appreciate that dispenser 10 can include openings that have a variety of configurations and which provide alternative mechanisms for accessing feeder mechanisms 24, including, for example, threaded openings, snap fit openings, frictional fit openings, tongue and groove opening, and combinations thereof.

Body 12 can, in one embodiment, be formed as a single piece with cavity 22 and feeding mechanism 24 formed integrally. After dispensing all the sensors from cavity 22, sensor dispenser 10 could be disposed. Alternatively, sensor dispenser 10 is refillable and includes a detachable storage area 18. When all the sensors in cavity 22 are dispensed, storage area 18 could be detached from the device and a new storage area 18 (containing sensors) could be attached to sensor dispenser 10 to refill the sensor dispenser. One skilled in the art will appreciate that storage area 18 can be mated with sensor dispenser 10 in a variety of ways, such as, for example, with a snap fit, threads, slot and grove, or a combination thereof.

In one aspect, elongate body 12 can include a window 30 that allows a user to visually estimate the number of sensors remaining in cavity 22. A visual inspection will allow a user to determine when the supply of sensors runs low. One skilled in the art will appreciate that alternatively, or in addition, a variety of counting mechanisms, including electrical and mechanical based counters, could be used to alert a user to the quantity of sensors remaining within cavity 22.

Figure 4:
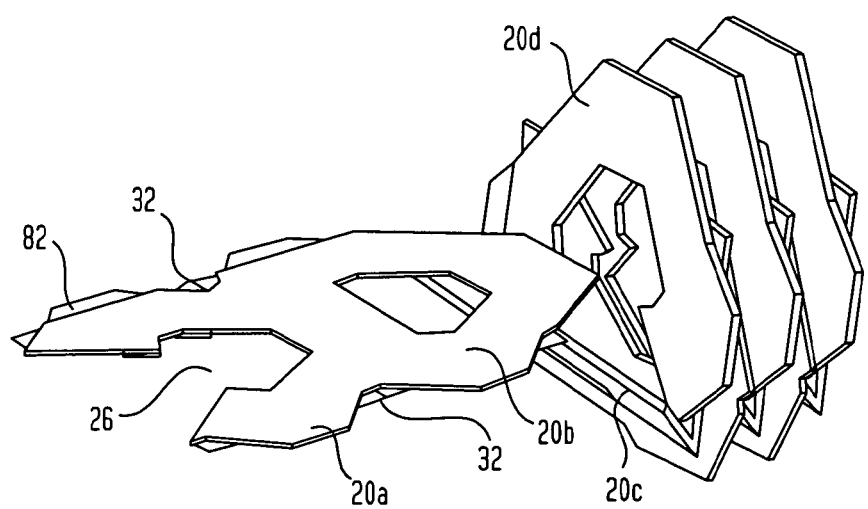
FIG. 4 illustrates an array of the sensors of FIG. 3 connective via flexible hinges.
Figure 5:
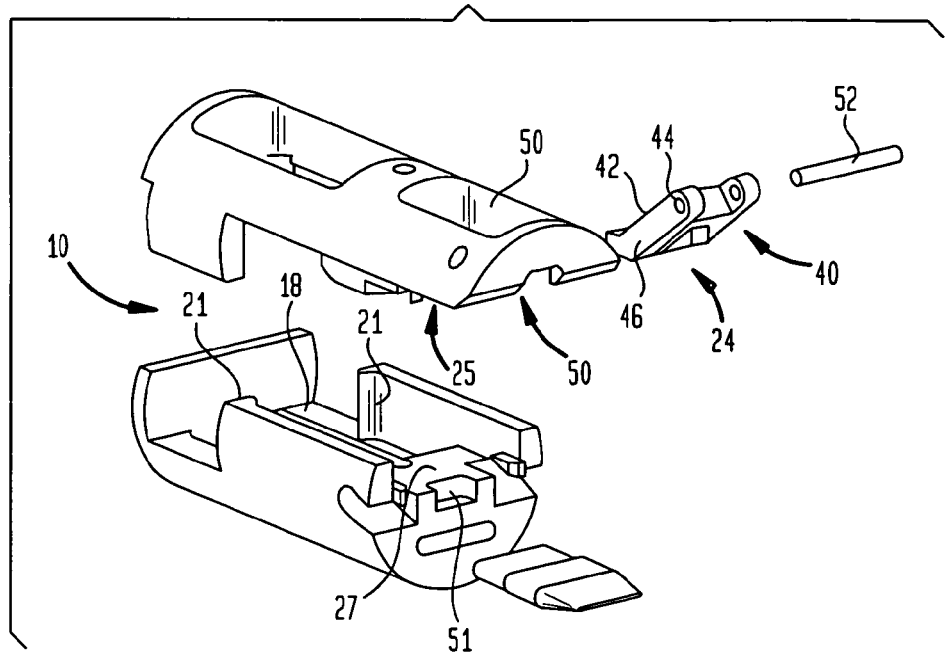
FIG. 5 is an exploded view of the sensor dispenser disclosed herein.

The interior of storage area 18 can have a shape adapted for the storage and delivery of sensors 20. For example, interior of cavity 22 can be shaped to hold a folded array of sensors like those illustrated in FIGS. 3 and 4. As shown, an array of sensors 20a, 20b, 20c, 20d, etc., are connected via flexible hinges 32. Sensors 20 can be folded at hinges 32 for storage in a folded stack and then unfolded for dispensing. At least a portion of storage area 18 can have a shape corresponding to the folded sensors. In addition, the interior walls of cavity 22 can include guide features 21 to assist with moving sensors 20 from cavity 22 to feeder mechanism 24. In one embodiment, storage area 18 includes guide features 21 to hold and/or directed sensors 20 prior to delivery to feeder mechanism 24. FIG. 5 illustrates guide features 21 defined by first and second protrusions that extend from the interior walls of storage area 18 and serve to contain the folded stack of sensors. As the sensors 20 are pulled during dispensing, the first sensor in the stack of folded sensors is pulled past the protrusions. In one aspect, protrusions are sized such that the sensors 20 slightly flex (i.e., bend) as they are pulled past the protrusions. The guide features 21 can thus keep the folded stack of sensors orderly and can provide an open area between the folded stack of sensors and feeder mechanism 24. This open area allows sensors to move into position for receipt by feeding mechanism 24 and helps to prevent jamming.

Feeding mechanism 24 can engage the first sensor in the array of sensors and can hold the sensor in position until a meter activates the feeding mechanism and allows the sensor to be dispensed. In one embodiment, feeding mechanism 24 hold a sensor in position by preventing proximal movement of the sensor. FIG. 5 illustrates an exploded view of sensor dispenser 10 including feeder mechanism 24 with a sensor engaging member 40 that can move between a sensor engaging position and a sensor dispensing position. When a meter engages dispenser 10, the sensor engaging member 40 is forced, by the meter, from the sensor engaging position to the sensor dispensing position. In the sensor dispensing position, the sensor is released by feeder mechanism 24 and can be dispensed.

Figure 6:
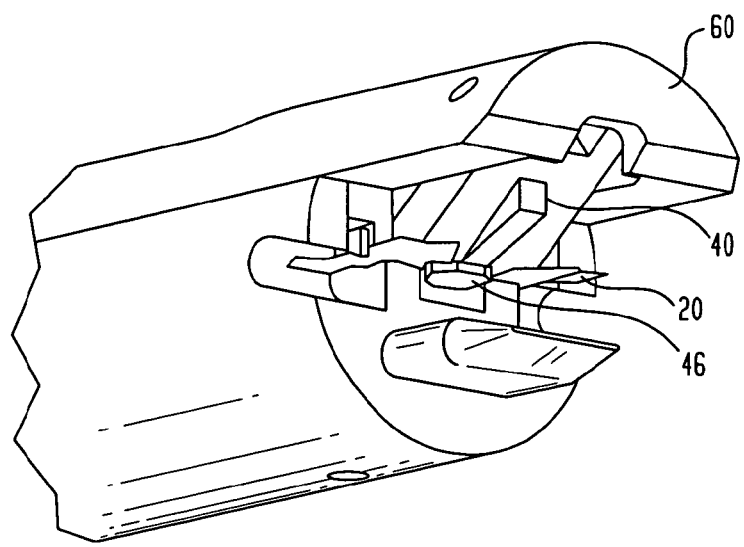
FIG. 6 is a partial perspective view of the dispensing end of the sensor dispenser.
Figure 7:
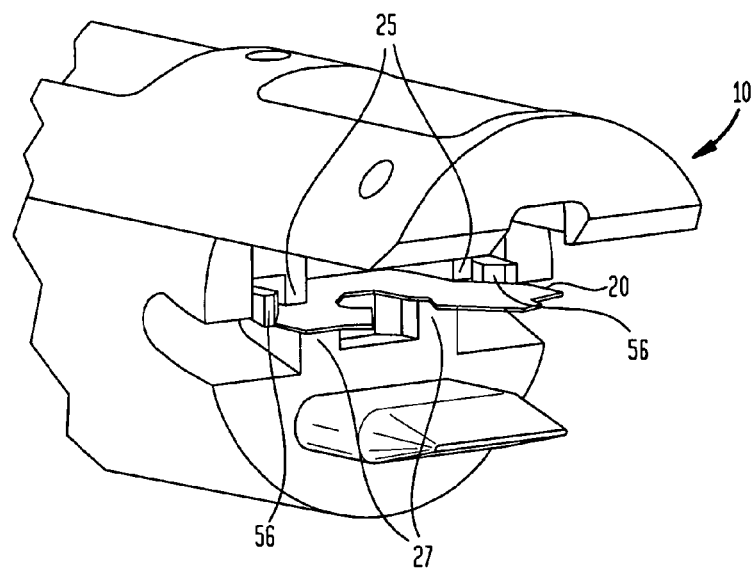
FIG. 7 illustrates the sensor dispenser of FIG. 6 in a dispensing configuration.

Sensor engaging member 40 can include an elongate body 42 with a first end 44 mated with body 12 and a second end 46 configured for mating with sensor 20. For example, second end 46 of sensor engaging member 40 can have a shape adapted to mate with a portion of sensor 12. One skilled in the art will appreciate that the configuration of the second end 46 of sensor engaging member 40 can depend on the features of the sensor and can be configured to hold a variety of differently shaped sensors.

Where a series of connected sensors are positioned within dispenser 10, the first sensor in the series can be prevented from dispensing by sensor engaging member 40. FIG. 6 shows sensor engaging member 40 in a sensor engaging position with second end 46 of engaging member 40 mated with sensor 20. In this position, sensor 20 cannot be dispensed. However, when a meter engages the proximal end of dispenser 10, the meter moves the sensor engaging member 40 into a sensor dispensing position. FIG. 7 illustrates sensor engaging member 40 in a dispensing position.

Figure 8A:
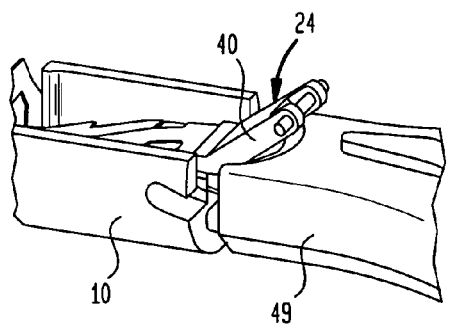
FIG. 8A is a cut-away view of the sensor dispenser partially engaged by a meter.
Figure 8B:
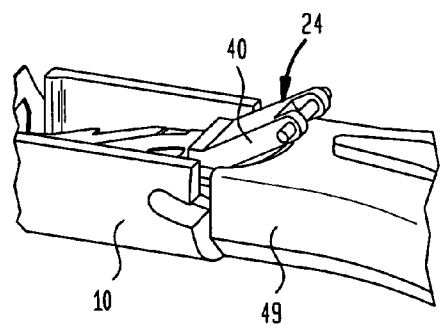
FIG. 8B is a cut-away view of the sensor dispenser of FIG. 8A with the sensor dispenser and meter fully engaged.

FIGS. 8A and 8B, illustrate a cut-away view of sensor dispenser 10 engaged with a meter 49. As meter 49 engages the proximal end of sensor dispenser 10 (feeder mechanism 24), the sensor engaging member 40 is lifted from the sensor engaging position by the force of meter 49 (FIG. 8B). Meter 49 can then mate with sensor 20.

Sensor engaging member 40, in one aspect, can be pivotally fixed to dispenser 10, such that the sensor engaging member can pivot between a sensor engaging position and a sensor dispensing position. In one embodiment (as shown in FIG. 5), a pivot pin 52 can pivotally fix engaging member 40 to body 12. One skilled in the art will appreciate that sensor engaging member 40 can be mated with body 12 in a variety of alternative ways that allow the sensor engaging member to move between a sensor engaging and a sensor dispensing position. In another exemplary embodiment, sensor engaging member 40 is fixedly mated to body 12 and is flexible. When a meter engages feeder mechanism 24, the meter bends sensor engagement member 40 and moves it from a sensor engaging position to a sensor dispensing position.

In one embodiment, engaging member 40 is biased in the sensor engaging position. The meter can move the sensor engaging member from a sensor engaging position to a sensor dispensing position, and then after the meter is removed, the engaging member returns to the sensor engaging position. For example, a spring can be positioned between body 12 and engaging member 40 to apply downward pressure. The spring allows the engaging member to travel upwards when contacted by the meter. When the meter is removed the action of the spring returns the engaging member to the sensor engaging position. In an alternative aspect the engaging member is resilient. For example, the engaging member can be fixedly mated with body 12 in the sensor engaging position. When the meter contacts the engaging member, the engaging member is bent upwards to allow for dispensing. When the meter is removed the resilient engaging member returns to its original position. Other exemplary means for biasing the engaging member include, for example, magnets and electromechanical actuators.

Dispenser 10 can include other feature to assist with dispensing sensor 20. In one aspect, the proximal surface of dispenser 10 includes stops 56 which prevent sensor 20 from retreating into the dispenser. Stops 56 allow sensor 20 to move in a proximal (dispensing) direction but limit (or prevent) distal movement. As the sensor travels into position in feeding mechanism 24, stops 56 contact the sides of sensor 20. In one embodiment, as shown in FIG. 7, stops 56 can have a taper that corresponds to a "V" shape of the sensor. When the sensor moves past the stops, the stops contact the sides of the sensor and prevent distal movement. One skilled in the art will appreciate that that configuration of the stops can be adapted to the shape of the sensor.

In one aspect, stops 56 cooperate with engaging member 40. When a sensor is engaged within feeder mechanism 24, stops 56 prevent distal movement while engaging member 40 prevents proximal movement. Together stops 56 and engaging member 40 can control the movement of sensor 20. Alternatively, engaging member 40 mates with sensor 20 such that it prevents both proximal and distal movement.

The sensor dispenser can include other features that work with feeder mechanism 24 to assist with dispensing sensors 20. For example, proximally positioned top and bottom interior surfaces 25 and 27 of body 12, respectively, can assist with directing the sensors into engagement with engaging mechanism 40. As shown in FIG. 5, surfaces 25 and 27 are generally flat and spaced apart a distance less than the height of storage chamber 18. As the connected sensors are pulled from the storage chamber, they encounter surfaces 25 and 27 and are directed into contact with the engagement mechanism. In one aspect, surface 25 and/or 27 are sloped to help direct sensor 20. For example, top surface 25 can slope downward and/or top surface 27 can slope upward to funnel sensors 20 into feeding mechanism 24.

In addition, top interior surface 25 can include a recess or opening 50 into which sensor engaging mechanism 40 can travel when the sensor engaging mechanism is in a sensor dispensing position (FIG. 1). Recess 50 allows the sensor dispensing mechanism to move out of the way of a sensor during the dispensing procedure. A second recessed 51 area can be positioned in the bottom interior surface 27 for receiving at least portion of engaging mechanism 40. The engaging member can be seated within recess 51 while in the sensor engaging position.

Dispenser 10, as described herein, can include alignment features that facilitate alignment of feeder mechanism 24 of dispenser 10 with meter 49. In particular, the alignment features can help bring meter 49 into contact with feeder mechanism 24 to activate the feeder mechanism. In addition, alignment features can help to orient and align a sensor mating mechanism 58 on meter 49 so that the sensor mating mechanism can receive a sensor dispensed from sensor dispenser 10. Exemplary alignment features can include, markers (colors, arrows, etc.) that indicate the orientation of the dispenser and/or surface contours that help guide meter 49 into contact with feeder mechanism 24.

Figure 9:
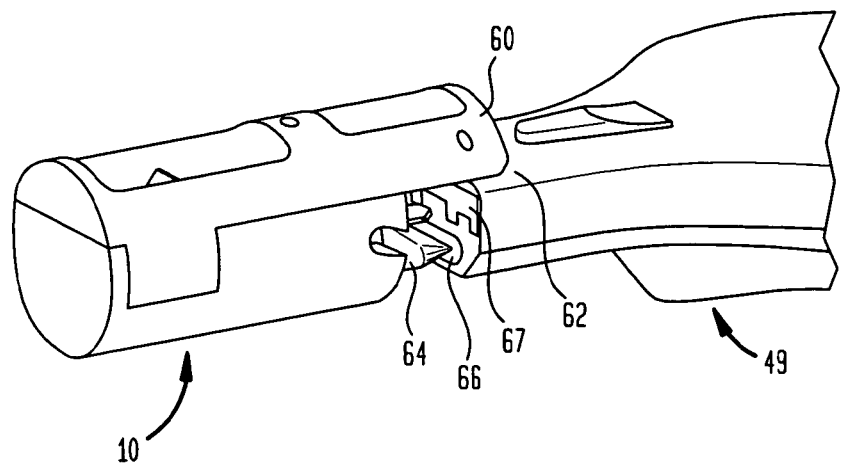
FIG. 9 is another view of the sensor dispenser and meter in a partially engaged configuration.

In one aspect, the proximal surface of dispenser 10 can be shaped to match a corresponding shape on meter 49. FIG. 9 illustrates the proximal surface of sensor dispenser 10 including an extension portion 60 that extends proximally and corresponds to an upper surface 62 on meter 49. In use, upper surface 62 of meter 49 slides under extension portion 60 and guides meter 49 into contact with feeder mechanism 24. In another aspect, sensor dispenser 10 includes a guide blade 64 that can mate with a recess 66 in meter 49 when the dispenser and meter are properly aligned. The proximal surface of guide blade 64 can be tapered to facilitate insertion of the guide blade into a recess within meter 49. In use, these alignment features will prevent sensor dispenser 10 and meter 49 from mating unless the feeder mechanism 24 and sensor mating mechanism 58 are properly aligned for dispensing a sensor. One skilled in the art will appreciate that sensor dispenser 10 and meter 49 can include a variety of features to assist with alignment.

In one embodiment described herein an electrochemical meter adapted for use with an electrochemical sensor is disclosed. The meter includes an area to receive a sensor to perform an electrochemical analysis including a mating mechanism 58 for mating with sensors dispensed from sensor dispenser 10. The mating mechanism is designed to hold and/or lock a sensor in position during analysis. For example, meter 49 can include a retention post 74 having a shape corresponding to at least a portion of sensor 20. When meter 49 is brought into contact with sensor 20, positioned in feeder mechanism 24, the sensor can be directed into an opening 72 and retention post 74 can mate with sensor 20. In one embodiment, meter 49 can mate with sensor 20 at the same time that dispenser 10 is mated with sensor 20. For example, retention post 74 can mate with a proximal portion of sensor 20 while feeder mechanism 24 mates with a distal portion of sensor 20. Bringing meter 49 fully into contact with feeder mechanism 24 then releases sensor 20 from feeder mechanism 24 while sensor 20 remains locked within meter 49. FIG. 11 shows sensor 20 positioned within meter 49 and retention post 74 locking sensor 20 in place.

Figure 10:
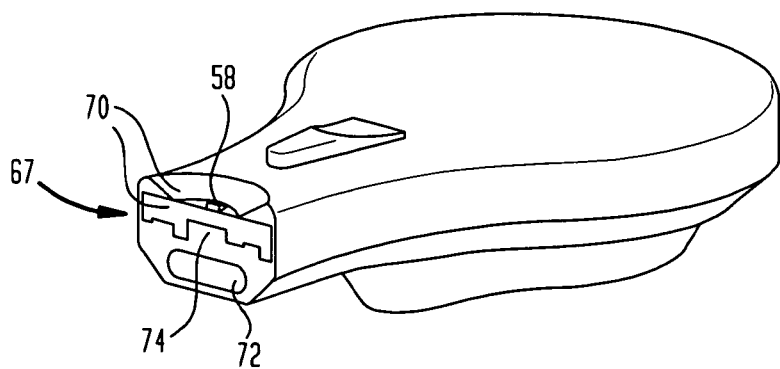
FIG. 10 is a perspective view of one embodiment of the meter disclosed herein and adapted for use with the sensor dispenser disclosed herein.

Meter 49 disclosed herein is also adapted to work with feeder mechanism 24. In one aspect, the distal surface of meter 49 includes a locating surface 70 for contacting feeder mechanism 24. As shown in FIG. 10, surface 70 is tapered and recessed so that as meter 49 is brought into contact with sensor dispenser 10, mating mechanism 58 contact sensor 20 prior to feeder mechanism 24 releasing the sensor. As meter 49 moves further into engagement, surface 70 will then contact engaging member 40 and move the engaging member into a sensor dispensing configuration. Depending on the positioning of the engaging member 40 and the configuration of surface 70, the mating mechanism can mate with sensor 20 either prior to, at the same time as, or after sensor dispenser releases sensor 10. In one embodiment, meter 49 and sensor dispenser 10 are configured such that feeder mechanism 24 and mating mechanism 58 mate with sensor 20 at the same time.

Distal surface 67 of meter 49 can include features that assist with directing sensor 20 into mating mechanism 58. For example, distal surface 67 of meter 49 can be tapered around opening 72 to help guide sensor 20 into sensor mating mechanism 58. FIG. 10 shows tapered lead-in surfaces on the distal surface of meter 49 that help seat sensor 20 within sensor mating mechanism 58.

The proximal portion of meter 49 can include a power source that can electrically communicate with sensor 20 and a processor for directing analysis, collecting data, and/or calculating a characteristic of an analyte (e.g., analyte concentration). In addition, meter 49 can include a screen for interfacing with a user. One skilled in the art will appreciate that meter 49 can be adapted for analyzing substances using a variety of circuit configurations, user interfaces, and calculation schemes. Exemplary, meter configuration are disclose for example in U.S. Pat. No. 6,475,372 to Ohara et al., and U.S. Pat. No. 5,942,102 to Hodges, et al., which are hereby incorporated by reference in their entirety.

In another embodiment disclosed herein, a method of using sensor dispenser 10 to dispense sensor 20 is disclosed. In one aspect, the method includes using meter 49 to activate sensor dispenser 24 and dispensing a sensor 20 from sensor dispenser 10 to meter 49. FIGS. 11A through 11D illustrate the operation of sensor dispenser 10 in feeding a sensor 20 to a meter 49.

Prior to delivery of a sensor, a user can first prepare dispenser 10 for operation by opening access to sensor feeding mechanism 24. For example, body 12 can include a resealable access port at a proximal end 14, such as an air tight cap (FIGS. 2A and 2B). Opening the proximal end of dispenser 10 provides access to the proximal surface of sensor feeding mechanism 24.

Figure 11A:
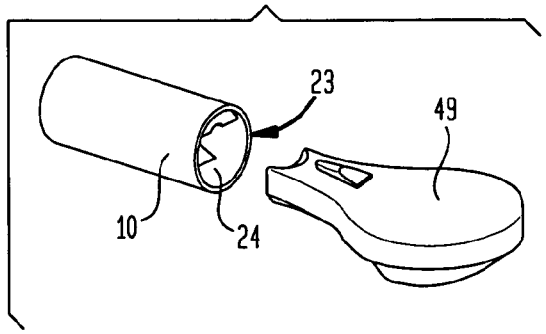
FIG. 11A is a perspective view of the sensor dispenser and meter.
Figure 11B:
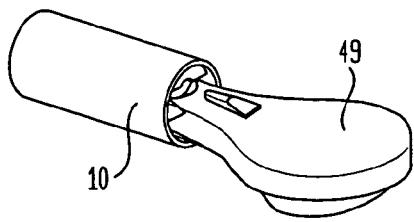
FIG. 11B is a perspective view of the meter inserted into the sensor dispenser.

A user can then align dispenser 10 with meter 49 and bring sensor feeding mechanism 24 into contact with sensor mating mechanism 58, for delivery of an individual sensor from sensor dispensing 10 to meter 49. FIG. 11A shows sensor dispenser 10 and meter 49 properly oriented and ready to engage one another. As dispenser 10 and meter 49 are brought together the alignment features discussed above can assist with fine tuning the alignment of feeder mechanism 24 and mating mechanism 58. FIG. 11B illustrates meter 49 engaged with sensor dispenser 10.

Figure 11C:
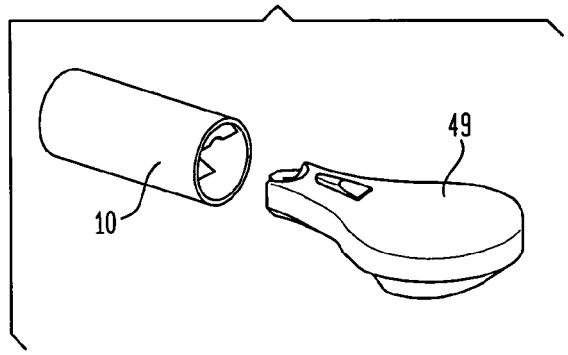
FIG. 11C is a perspective view of the sensor dispenser and the meter with a dispensed sensor.

In one aspect, an array of connected sensors are positioned within dispenser 10, with feeding mechanism 24 holding or locking a first sensor in place until the insertion of meter 49 into dispenser 10 actives feeder mechanism 24. In one aspect, feeding mechanism 24 prevent proximal movement, while stops 56 contact sensor 20 and prevent the sensor from moving distally. The sensor is also constrained by upper and lower surfaces 25, 27. Contacting feeder mechanism 24 with meter 49 releases sensor 20 from feeder mechanism 24, while the mating mechanism 58 of meter 49 engages the sensor. As sensor 20 is released from dispenser 10, mating mechanism 58 locks the sensor within meter 49. Separating meter 49 from dispenser 10 can tear the sensor away from the array of connected sensors and can pull the next sensor into engagement with feeder mechanism 24. FIG. 11C illustrates meter 49 with a dispensed sensor 20 locked in mating mechanism 58.

Figure 11D:
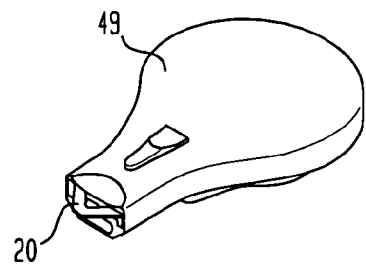
FIG. 11D is a perspective view of the meter disclosed herein including a sensor positioned therein.

Once sensor 20 is mated with meter 49, a user can deliver a sample of physiological fluid to the sensor and perform an analysis. In one aspect, sensor 20 and meter 49 are used to determine the concentration of glucose in whole blood. The user delivers a sample (e.g., a whole blood sample) into a reaction chamber within the sensor, and the sample can react with a reagent and electrodes positioned therein. The meter creates an electrical potential across the electrodes and collects data (e.g., time and current data). Based on the collected data the meter can provide the user with information about an analyte within the sample (e.g., glucose concentration). FIG. 11D illustrates sensor 20 ready to receive a sample.

Figure 12A:
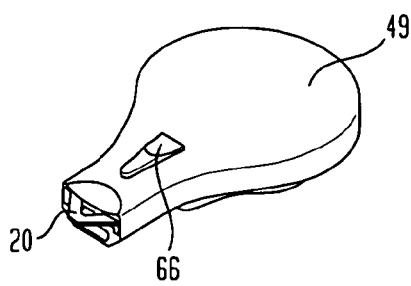
FIG. 12A is a perspective view of the meter with a sensor locked therein.
Figure 12B:
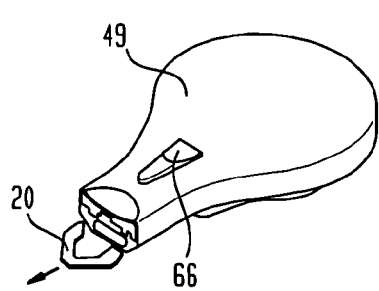
FIG. 12B is a perspective view of the sensor and meter of FIG. 12A with the sensor being ejected from the meter.

Sensor 20 is generally intended for a single use and can be disposed after analysis. For example, as shown in FIGS. 12A and 12B, after completion of the test, the user can eject the spent sensor. In one embodiment, sensor 20 is ejected from meter 49 by depressing and/or advancing an ejection button 66. The testing procedure can be repeated, as desired, by feeding another sensor to meter 49 from sensor dispenser 10.

Figure 3:
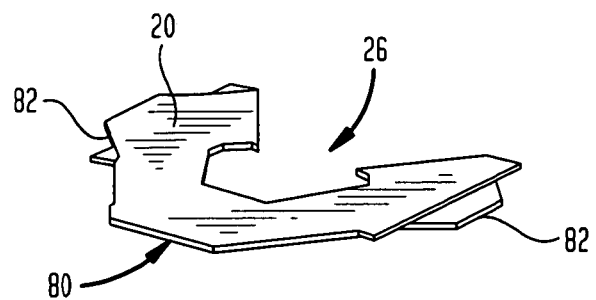
FIG. 3 is a perspective view of an exemplary sensor for use with the sensor dispenser.

The sensor used with sensor dispenser 10 can, in one embodiment, be an electrochemical sensor having spaced apart electrodes that define a reaction chamber. The sensor can further include electrical contacts, positioned on the surface of the sensor, which are in electrical contact with the electrodes. These contacts allow a meter to electrically communicate with the electrodes positioned within the reaction chamber. FIGS. 3 and 4 illustrates one exemplary embodiment of a generally "V" shaped sensor that can be used with dispenser 10 and that includes a longitudinal reaction chamber 80 with laterally spaced electrical contacts 82. In one aspect, reaction chamber 80 is positioned toward a distal end of the sensor and electrical contacts 82 are positioned toward a proximal end of the sensor. The sensor can be dispensed proximal end first so that the meter receives the electrical contacts.

Sensor 20 can also include features that assist with dispensing. For example, sensor 20 illustrated in FIGS. 3 and 4 including a open region 26 that can receive at least a portion of sensor dispenser 10. As described above, dispenser 10 and meter 49 can mate with surface features, such as open region 26, for holding and/or dispensing the sensor. One skilled in the art will appreciate that sensor 20 can include a variety of other features for mating with dispenser 10, such as, for example, notches in the side of the sensor, apertures through the sensor, recesses or protrusions on the sensor, and combinations thereof.

Sensor 20, in one embodiment, is part of an array of connected sensors (20a, 20b, 20c, etc.). The sensors can be folded into a space-efficient configuration for storage in sensor dispenser 10. In one aspect, an array of fan folded sensors are positioned within dispenser 10 and individually dispensed. The connection 32 between sensors allows the sensors to be stored in a folded configuration and then pivoted into a planer configuration for dispensing. Once the meter mates with the sensor during the dispensing process, the connection can be broken (e.g., torn) to allow the sensor to be dispensed.

One skilled in the art will appreciate that sensor 20 can include the variety of electrochemical sensors capable of being dispensed from a dispenser. Exemplary sensors are described in a United States patent application entitled "Method and Apparatus for Electrochemical Analysis" filed on the same date as this application, and incorporated herein by reference in its entirety.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An electrochemical sensor dispenser device, comprising:
    an elongate body having a proximal and distal end, the elongate body further including a proximally positioned dispensing surface with an opening for dispensing an electrochemical sensor, the proximal end of the elongate body being configured for releasable axial engagement with a distal end of a test meter;
    a distally positioned chamber adapted for the storage of a series of electrochemical sensors;
    a sensor feeder mechanism disposed at the proximal end of said sensor dispenser device, the feeder mechanism including an elongate member having a first end and second end, the second end being adapted to move between a sensor engaging position and a sensor feeding position, the elongate member biased in the sensor engaging position prior to engagement with the test meter; and
    a mechanism enabling releasable engagement between the proximal end of the sensor dispenser device and the distal end of a test meter for engaging and receiving a sensor from the dispenser device and in which the mechanism enabling releasable engagement is configured to automatically cause the elongate member to be moved from the sensor engaging position to the sensor feeding position when the proximal end of the dispensing device is engaged with a test meter.

2. The device of claim 1, wherein the elongate member of the feeder mechanism is pivotally secured to the elongate body at the first end.

3. The device of claim 1, wherein the elongate member of the feeder mechanism is fixedly secured to the first body at the first end and is flexible.

4. The device of claim 1, wherein the second end of the elongate member of the feeder mechanism is adapted to mate with a sensor.

5. The device of claim 4, wherein the second end of the elongate member of the feeder mechanism has a shape that is complementary to an open region on a sensor.

6. The device of claim 1, further comprising stops positioned proximate to the opening and adapted to resist movement of a sensor in a distal direction.

7. The device of claim 1, wherein the body includes alignment features to facilitate alignment of the device with a meter, separately engaged with the dispenser device.

8. The device of claim 7, wherein a portion of the proximally positioned dispensing surface extends beyond the sensor feeding mechanism to provide an alignment surface.

9. The device of claim 1, wherein the body includes a window for visually inspecting the storage chamber.

10. The device of claim 1, wherein the body provides a generally air-tight enclosure of the storage chamber.

11. The device of claim 1, further comprising a resealable opening at the proximal end.

12. The device of claim 11, wherein opening the resealable opening provides access to the proximally positioned dispensing surface.

13. The device of claim 1, wherein a series of connected sensors are positioned within the storage chamber.

14. The device of claim 13, wherein at least a portion of the sensors are stored in the sensor storage area in a folded configuration.

15. The device of claim 13, wherein the storage chamber includes guide features adapted to restrain a stack of folded sensors.

16. A system for delivering an electrochemical sensor to a meter, comprising:
- a sensor dispensing device having an elongate body including a sensor storage area and a sensor dispensing mechanism disposed therein, the sensor dispensing mechanism including an elongate member being adapted to move between a sensor dispensing position and a sensor engaging position; and
- a meter adapted to receive a sensor from said sensor dispensing mechanism, the meter having a distal end releasably engageable with a proximal end of the sensor dispensing device and including a surface adapted to engage the sensor dispensing mechanism and automatically move the elongate member from the sensor dispensing position to the sensor engaging position upon axial engagement between the proximal end of the dispensing device and the distal end of the meter, the meter further including a sensor mating mechanism that can mate with a sensor moved to the sensor dispensing position based on axial engagement of the meter therewith.

17. The system of claim 16, wherein the sensor mating mechanism is adapted to lock a dispensed sensor in the meter.

18. The system of claim 16, further including a series of connected sensors in the sensor storage area.

19. The system of claim 17, wherein at least a portion of the sensors are stored in the sensor storage area in a folded configuration.

20. The system of claim 17, wherein the sensors each have a longitudinal reaction chamber and laterally spaced electrical contact areas.

21. The system of claim 20, wherein the meter includes laterally spaced electrical contactors adapted to electrically communicate with the laterally spaced contact areas on the sensor.

22. The system of claim 16, wherein the sensor dispenser includes a dispensing surface that is complementary to a surface on the releasably attachable meter.

23. The system of claim 16, wherein the sensor dispenser includes alignment features that are complementary to a surface on the meter.

24. An electrochemical sensor dispenser device, comprising:
- an elongate cylindrical body having a distal end and a proximal end, the proximal end being configured for axially engaging the distal end of a test meter;
- a distal sensor storage chamber retaining at least one electrochemical sensor, the at least one sensor including a longitudinal reaction chamber, two electrical contact areas, and a sensor dispenser mating area; and
- a proximal sensor feeder mechanism adapted to mate with a sensor retained in said distal storage chamber, the feeder mechanism including an elongate member having a first end and second end, the second end of the elongate member being adapted to pivot between a sensor engaging position and a sensor feeding position automatically upon engagement of the proximal end of the device with the distal end of a test meter, the elongate member being initially biased in the sensor engaging position.

25. The device of claim 24, wherein the second end of the elongate member has a shape that is complementary to the sensor dispensing mating area on the sensor.

* * * * *